United States Patent
Pettis et al.

(10) Patent No.: US 9,192,750 B2
(45) Date of Patent: Nov. 24, 2015

(54) METHOD AND DEVICE FOR CONTROLLING DRUG PHARMACOKINETICS

(75) Inventors: Ronald J. Pettis, Cary, NC (US); Noel Harvey, Efland, NC (US); Barry Ginsberg, Wyckoff, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 156 days.

(21) Appl. No.: 12/755,540

(22) Filed: Apr. 7, 2010

(65) Prior Publication Data

US 2010/0262120 A1    Oct. 14, 2010

Related U.S. Application Data

(62) Division of application No. 10/429,973, filed on May 6, 2003, now Pat. No. 7,722,595.

(60) Provisional application No. 60/377,649, filed on May 6, 2002, provisional application No. 60/389,881, filed on Jun. 20, 2002.

(51) Int. Cl.
*A61M 31/00* (2006.01)
*A61M 37/00* (2006.01)

(52) U.S. Cl.
CPC ... *A61M 37/0015* (2013.01); *A61M 2037/0023* (2013.01); *A61M 2037/0061* (2013.01)

(58) Field of Classification Search
CPC ............... A61M 37/0015; A61M 2037/0023; A61M 2037/0061
USPC ......... 604/500, 173, 22, 20, 27, 28, 239, 117, 604/506, 522, 141, 180, 272
See application file for complete search history.

(56) References Cited

U.S. PATENT DOCUMENTS

| | | | |
|---|---|---|---|
| 2,619,962 A | 12/1952 | Rosenthal | |
| 3,467,096 A * | 9/1969 | Horn | 604/173 |
| 3,814,097 A | 6/1974 | Ganderton et al. | |
| 3,964,482 A | 6/1976 | Gerstel et al. | |
| 4,270,537 A | 6/1981 | Romaine | |
| 4,435,173 A * | 3/1984 | Siposs et al. | 604/155 |
| 4,592,753 A | 6/1986 | Panoz | |
| 4,886,499 A | 12/1989 | Cirelli et al. | |
| 5,003,987 A | 4/1991 | Grinwald | |
| 5,098,389 A | 3/1992 | Cappucci | |

(Continued)

FOREIGN PATENT DOCUMENTS

| | | |
|---|---|---|
| CA | 2 349 431 | 5/2000 |
| EP | 0 205 915 | 12/1986 |

(Continued)

OTHER PUBLICATIONS

"Flu vaccine: skin injection method effective in younger people," *American Health Line: Research Notes* (Nov. 4, 2004).

(Continued)

*Primary Examiner* — Edelmira Bosques
*Assistant Examiner* — Bradley G Thomas, Jr.
(74) *Attorney, Agent, or Firm* — The Webb Law Firm

(57) ABSTRACT

Methods and devices for administration of substances into at least two compartments of skin for systemic absorption and improved pharmacokinetics, based on biphasic or bimodel kinetic profiling.

7 Claims, 5 Drawing Sheets

(56) References Cited

U.S. PATENT DOCUMENTS

| | | | |
|---|---|---|---|
| 5,156,591 A | | 10/1992 | Gross et al. |
| 5,169,390 A | * | 12/1992 | Athayde et al. ............... 604/141 |
| 5,250,023 A | | 10/1993 | Lee et al. |
| 5,279,544 A | | 1/1994 | Gross et al. |
| 5,279,552 A | | 1/1994 | Magnet |
| 5,417,662 A | | 5/1995 | Hjertman et al. |
| 5,527,288 A | | 6/1996 | Gross et al. |
| 5,582,591 A | | 12/1996 | Cheikh |
| 5,591,139 A | | 1/1997 | Lin et al. |
| 5,801,057 A | | 9/1998 | Smart et al. |
| 5,820,622 A | | 10/1998 | Gross et al. |
| 5,848,990 A | | 12/1998 | Cirelli et al. |
| 5,848,991 A | | 12/1998 | Gross et al. |
| 5,876,582 A | | 3/1999 | Frazier |
| 5,879,326 A | | 3/1999 | Godshall et al. |
| 5,928,207 A | | 7/1999 | Pisano et al. |
| 5,957,895 A | | 9/1999 | Sage et al. |
| 5,997,501 A | * | 12/1999 | Gross et al. ...................... 604/65 |
| 6,017,328 A | * | 1/2000 | Fischell et al. ................. 604/180 |
| 6,056,716 A | | 5/2000 | D'Antonio et al. |
| 6,099,504 A | | 8/2000 | Gross et al. |
| 6,200,291 B1 | | 3/2001 | Di Pietro |
| 6,261,272 B1 | * | 7/2001 | Gross et al. .................... 604/272 |
| 6,319,224 B1 | | 11/2001 | Stout et al. |
| 6,334,856 B1 | | 1/2002 | Allen et al. |
| 6,346,095 B1 | | 2/2002 | Gross et al. |
| 6,482,176 B1 | | 11/2002 | Wich |
| 6,494,865 B1 | | 12/2002 | Alchas |
| 6,565,532 B1 | | 5/2003 | Yuzhakov |
| 6,572,545 B2 | * | 6/2003 | Knobbe et al. ................. 600/365 |
| 6,607,513 B1 | | 8/2003 | Down et al. |
| 6,623,457 B1 | | 9/2003 | Rosenberg |
| 2001/0012926 A1 | | 8/2001 | Gross et al. |
| 2002/0038111 A1 | * | 3/2002 | Alchas et al. ................. 604/500 |
| 2002/0095124 A1 | | 7/2002 | Palasis et al. |
| 2002/0095134 A1 | * | 7/2002 | Pettis et al. ................... 604/506 |
| 2002/0156453 A1 | | 10/2002 | Pettis et al. |
| 2002/0193729 A1 | | 12/2002 | Cormier et al. |
| 2002/0193778 A1 | | 12/2002 | Alchas et al. |
| 2003/0073609 A1 | | 4/2003 | Pinkerton |
| 2003/0083618 A1 | * | 5/2003 | Angel et al. ................... 604/141 |
| 2003/0083641 A1 | * | 5/2003 | Angel et al. ................... 604/500 |
| 2003/0083645 A1 | * | 5/2003 | Angel et al. ................. 604/890.1 |
| 2004/0028707 A1 | | 2/2004 | Pinkerton |
| 2004/0073160 A1 | | 4/2004 | Pinkerton |
| 2004/0170654 A1 | | 9/2004 | Pinkerton |
| 2004/0175401 A1 | | 9/2004 | Pinkerton |
| 2005/0137531 A1 | | 6/2005 | Prausnitz et al. |

FOREIGN PATENT DOCUMENTS

| | | |
|---|---|---|
| EP | 0 429 842 | 8/1996 |
| EP | 1 086 718 | 3/2001 |
| EP | 1 086 719 | 3/2001 |
| EP | 1 088 642 | 4/2001 |
| EP | 1 092 444 | 4/2001 |
| WO | WO 94/20076 | 9/1994 |
| WO | WO 94/23777 | 10/1994 |
| WO | WO 96/17648 | 6/1996 |
| WO | WO 96/37155 | 11/1996 |
| WO | WO 96/37256 | 11/1996 |
| WO | WO 97/21457 | 6/1997 |
| WO | WO 99/43350 | 9/1999 |
| WO | WO 99/64580 | 12/1999 |
| WO | WO 00/09186 | 2/2000 |
| WO | WO 00/67647 | 11/2000 |
| WO | WO 00/74763 | 12/2000 |
| WO | WO 01/78754 A2 | 10/2001 |
| WO | WO 01/91846 A2 | 12/2001 |
| WO | WO 02/02179 A1 | 1/2002 |
| WO | WO 02/11669 | 2/2002 |
| WO | WO 02/34241 A2 | 5/2002 |
| WO | WO 02/833232 | 10/2002 |
| WO | WO 03/002175 | 1/2003 |

OTHER PUBLICATIONS

Agrawal et al., "Pharmacokinetics, biodistribution, and stability of oligodeoxynucleotide phosphorothioates in Mice," *Proc. Natl. Acad. Sci. USA* 88:7595-7599 (1991).

Autret et al., "Comparaison des concentrations plasmatiques et de la tolérance d'une dose unique de calcitonine humaine administree," *Therapie* 46:5-8 (1991).

Autret et al., "Comparison of pharmacokinetics and tolerance of calcitonine administered by intradermal or subcutaneous route," *Fundamental Clinical Pharmacology* 3(2):170-171 (1989).

Bader, "Influenza vaccine experience in Seattle," *Am. J. Public Health* 70(5):545 (1980).

Belshe et al., "Serum antibody responses after intradermal vaccination against influenza," *New England Journal of Medicine* 351(22):2286-2294 (2004).

Benoni et al., "Distribution of Ceftazidime in Ascitic Fluid, Antimicrobial Agents and Chemotherapy," 25(6):760-763 (1984).

Bickers et al., editors, "Glucocorticosteroids," *Clinical Pharmacology of Skin Disease* 57-90, Churchill Livingstone, Inc. (1984).

Bocci et al., "The lymphatic route. IV. pharmacokinetics of human recombinant interferon a2 and natural interferon beta administered intradermally in rabbits," *International Journal of Pharmaceutics* 32:103-110 (1986).

Branswell, "Vaccine stretching may be an option for future shortages, pandemics: studies," *Canadian Press News Wire* (Nov. 3, 2004).

Bressolle et al., "A Weibull distribution model for intradermal administration of Ceftazidime," *Journal of Pharmaceutical Sciences* 82(11):1175-1178 (1993).

Bronaugh et al., "Methods for in vitro percutaneous absorption studies. II. animal models for human skin," *Toxicol Appl. Pharmacol.* 62(3):481-488 (1982).

Brooks et al., "Intradermal administration of bivalent and monovalent influenza vaccines." *Ann. Allergy. Aug.* 39(2):110-112 (1977).

Brown et al., "The immunizing effect of influenza A/New Jersey/76 (Hsw1N1) virus vaccine administered intradermally and intramuscularly to adults." *J. Infect. Dis.*136 Suppl:S466-71 (1977).

Burkoth et al., Transdermal and transmucosal powdered drug delivery, critical Review™ in therapeutic drug carrier systems 16 (4):331-384 (1999).

Callen, "Intralesional corticosteriods," *Journal of the American Academy of Dermatology, University of Louisville School of Medicine* 149-151 (1981).

Corbo et al., "Transdermal controlled delivery of propranolol from a multilaminate adhesive device." *Pharm Res.* 6(9):753-758 (1989).

Cossum et al., "Disposition of the c-labeled phosphorothioate oligonucleotide ISIS 2105 after intravenous administration to rats," *The Journal of Pharmacology and Experimental Therapeutics* 267(3):1181-1190 (1993).

Cossum et al., "Pharmacokinetics of c-labeled phosphorothioate oligonucleotide, ISIS 2105 after administration to rats," *The Journal of Pharmacology and Experimental Therapeutics* 269(1):89-94 (1994).

Crooke et al., "A pharmacokinetic evaluation of c-labeled afovirsen sodium in patients with genital warts," *Clinical Pharmacology & Therapeutics* 56(6):641-646 Dec. (1994).

Crowe, "Experimental comparison of intradermal and subcutaneous vaccination with influenza vaccine," *Am. J. Med. Technol.* 31(6):387-96 (1965).

Firooz, et al., "Benefits and risks of intralesional corticosteroid injection in the treatment of dermatological diseases," *Clinical and Experimental Dermatology* 20(5):363-370 (1995).

Fjerstad, "U. Minnesota professor uses alternative flu vaccine technique," *FSView & Florida Flambeau via U-Wire* (Nov. 15, 2004).

Foy et al., "Efficacy of intradermally administered A2 Hong Kong vaccine," *JAMA* 213(1):130 (1970).

Glenn et al., "Advances in vaccine delivery: transcutaneous immunisation." *Exp. Opin. Invest. Drugs* 8(6):797805 (1999).

Goodarzi et al., "Organ distribution and stability of phosphorothioated oligodeoxyribonucleotides in mice," *Biopharmaceutics & Drug Disposition* 13(3):221-227 (1992).

(56) References Cited

OTHER PUBLICATIONS

Gramzinski et al. "Immune response to a hepatitis B DNA vaccine in Aotus monkeys: a comparison of vaccine formulation, route, and method of administration," *Mol. Med.* 4(2):109-18 (1998).

Halperin et al., "A comparison of the intradermal and subcutaneous routes of influenza vaccination with A/New Jersey/76 (swine flu) and A/Victoria/75: report of a study and review of the literature," *Am. J. Public Health.* 69(12):1247-1251 (1979).

Haynes et al., "Ultra-long-duration local anesthesia produced by injection of lecithin-coated methoxyflurane microdroplets," *Anesthesiology* 63(5):490-499 (1985).

Henry et al., "Microfabricated microneedles: a novel approach to transdermal drug delivery," *Journal of Pharmaceutical Sciences* 87(8):922-925 (1998).

Herbert et al., "Comparison of responses to influenza A/New Jersey/76-A/Victoria/75 virus vaccine administered intradermally or subcutaneously to adults with chronic respiratory disease," *J. Infect. Dis.* 140(2):234-238 (1979).

Jakobson et al., "Variations in the blood concentration of 1,1,2-tricholoroethane by percutaneous absorption and other routes of administration in the guinea pig," *Acta Pharmacologizca et Toxicologica* 41(5):497-506 (1977).

Jarratt et al., "The effects of intradermal steroids on the pituitary-adrenal axis and the skin," *The Journal of Investigative Dermatology* 62(4):463-466 (1974).

Kaushik et al., "Transdermal Protein Delivery Using Microfabricated Microneedles," (1 page) (1999).

Kenney et al., "Dose sparing with intradermal injection of influenza vaccine," *New England Journal of Medicine* 351(22):2295-2301 (2004).

Kirkpatrick et al., "Local aesthetic efficacy of methoxyflurane microdroplets in man," *Anesthesiology* 67(3A):254 (1987).

Knox et al. "New research shows intradermal rather than intramuscular vaccine injection could stretch flu vaccine supplies," *National Public Radio: All Things Considered* (Nov. 3, 2004).

Kohn, "Flu shot technique yields more doses, studies find; critics say injecting skin rather than muscle is too difficult for common use," *The Baltimore Sun: Telegraph 3A* (Nov. 4, 2004).

Leroy et al., "Pharmacokinetics of ceftazidime in normal and uremic subjects," *Antimicrobal Agents and Chemotherapy* 25(5):638-642 (1984).

Majeski et al., "Technique could stretch vaccine; changing the way shots are given means the current supply of flu vaccine could immunize 10 times as many people, two Minnesota physicians say" *Saint Paul Pioneer Press: Main 1A* (Oct. 27, 2004).

Majeski, "Alternate flu shot less effective in elderly; doctors proposed method to stretch vaccine supply," *Saint Paul Pioneer Press: Main* 17A (Nov. 4, 2004).

Márián et al., "Hypoglycemia activates compensatory mechanism of glucose metabolism of brain," *Acta Biologica Hungarica* 52(1):35-45 (2001).

McAllister, et al., "Solid and Hollow Microneedles for transdermal protein delivery," *Proceed. Int'l. Symp. Control. Rel. Bioact. Mater. Controlled Release Society.* 26:192-193 (1999).

McAllister et al., "Three-dimensional hollow microneedle and microtube arrays," *Solid-State Sensors and Actuators Transducers-Conference*; 1098-1103 (1999).

McElroy et al., "Response to intradermal vaccination with A2, Hong Kong variant, influenza vaccine." *N. Engl. J. Med.* 281(19):1076 (1969).

McGugan et al., "Adrenal suppression from intradermal triamcinolone," *The Journal of Investigative Dermatology* 40:271-272 (1963).

Merriam-Webster's Collegiate Dictionary, 10$^{th}$ Edition, 1998, Merriam-Webster, Inc., Springfield, MA, p. 306.

Montagne et al., "Intradermal influenza vaccination—can less be more?" *New England Journal of Medicine* 351(22):2330-2332 (2004).

Niculescu et al., "Efficacy of an adsorbed trivalent split influenza vaccine administered by intradermal route." *Arch. Roum. Path. Exp. Microbiol.* 40(1):67-70 (1981).

Payler DK. "Intradermal influenza vaccine using Portojet 1976," *Br. Med. J.* 2(6095):1152 (1977).

Payler et al. "Intradermal influenza vaccination," *Br. Med J.* 2(921):727 (1974).

Rindfleisch et al., "La Crosse finding could curtail flu vaccine shortages," *Wisconsin State Journal* D9 (Nov. 14, 2004).

Scott et al., "Toxicity of Interferon," *British Medical Journal* 282:1345-1348 (1981).

Shute, "Second thoughts on the flu vaccine," *Science & Society; Public Health* 137(17):80.

Smith, "Low-dose vaccine helps block flu, study says younger adults seen benefiting," *The Boston Globe: National/Foreign A2* (Nov. 4, 2004).

Supersaxo et al., "Recombinant human interferon Alpha-2a: delivery to lymphoid tissue by selected modes of application," *Pharmaceutical Research* 5(8):472-476 (1998).

Sutherest, "Treatment of pruritus vulvae by multiple intradermal injections of alcohol. a double-blind study," *British Journal of Obstetrics and Gynecology* 86:371-373 (1979).

Sveinsson, "Investigation on the influence of insulin and adrenalin in rabbits with alimentary fatty liver and muscles and on the content of fat and sugar in blood," 8:66-86 (1939).

Tauraso et al., "Effect of dosage and route of inoculation upon antigenicity of inactivated influenza virus vaccine (Hong Kong strain) in man," *Bull. World Health Organ.* 41(3):507-16 (1969).

The American Heritage College Dictionary, 2000, 3$^{rd}$ Edition; Houghton Mifflin Company, Boston, New York, p. 368.

The Merck Manual of Diagnosis and Therapy, 1999, 17$^{th}$ Edition, Beers & Berkow, ed., Merck Research Laboratories, Division of Merck & Co., Inc., Whitehouse Station, NJ, pp. 2555-2571.

Ward et al., "Puritus vulvae: treatment by multiple intradermal alcohol injections," *British Journal of Dermatology* 93(2):201-204 (1975).

Wu et al., "Pharmacokinetics of methoxyflurane after its intra-dermal injection as lecithin-coated microdroplets," *Journal of Controlled Release* 9:1-12 (1989).

Zaynoun et al., "The effect of intracutaneous glucocorticoids on plasma cortisol levels," *British Journal of Dermatology* 88(2):151-156 (1973).

\* cited by examiner

METHOD AND DEVICE FOR CONTROLLING DRUG PHARMACOKINETICS

CROSS-REFERENCE TO RELATED APPLICATIONS

This application is a divisional of U.S. Ser. No. 10/429,973, filed May 6, 2003, which claims the benefit of U.S. Provisional Application No. 60/377,649, filed May 6, 2002 and U.S. Provisional Application No. 60/389,881, filed Jun. 20, 2002, each of which are herein incorporated by reference in their entirety.

BACKGROUND OF THE INVENTION

1. Field of the Invention

This invention relates to methods and devices for administration of substances into at least two compartments of skin for systemic absorption and improved pharmacokinetics.

2. Background Information

The importance of efficiently and safely administering pharmaceutical substances such as diagnostic agents and drugs has long been recognized. Although an important consideration for all pharmaceutical substances, obtaining adequate bioavailability of large molecules such as proteins that have arisen out of the biotechnology industry has recently highlighted this need to obtain efficient and reproducible absorption (Cleland et al., Curr. Opin. Biotechnol. 12: 212-219, 2001). The use of conventional needles has long provided one approach for delivering pharmaceutical substances to humans and animals by administration through the skin. Considerable effort has been made to achieve reproducible and efficacious delivery through the skin while improving the ease of injection and reducing patient apprehension and/or pain associated with conventional needles. Furthermore, certain delivery systems eliminate needles entirely, and rely upon chemical mediators or external driving forces such as iontophoretic currents or thermal poration or sonophoresis to breach the stratum corneum, the outermost layer of the skin, and deliver substances through the surface of the skin. However, such delivery systems do not reproducibly breach the skin barriers or deliver the pharmaceutical substance to a given depth below the surface of the skin and consequently, clinical results can be variable. Thus, mechanical breach of the stratum corneum such as with needles, is believed to provide the most reproducible method of administration of substances through the surface of the skin, and to provide control and reliability in placement of administered substances.

Approaches for delivering substances beneath the surface of the skin include subcutaneous, intramuscular or intravenous routes of administration of which, intramuscular (IM) and subcutaneous (SC) injections have been the most commonly used.

Anatomically, the outer surface of the body is made up of two major tissue layers, an outer epidermis and an underlying dermis, which together constitute the skin (for review, see *Physiology, Biochemistry, and Molecular Biology of the Skin, Second Edition*, L. A. Goldsmith, Ed., Oxford University Press, New York, 1991). The epidermis is subdivided into five layers or strata of a total thickness of between 75 and 150 µm. Beneath the epidermis lies the dermis, which contains two layers, an outermost portion referred to as the papillary dermis and a deeper layer referred to as the reticular dermis. The papillary dermis contains vast microcirculatory blood and lymphatic plexuses. In contrast, the reticular dermis is relatively acellular and avascular and made up of dense collagenous and elastic connective tissue. Beneath the epidermis and dermis is the subcutaneous tissue, also referred to as the hypodermis, which is composed of connective tissue and fatty tissue. Muscle tissue lies beneath the subcutaneous tissue.

As noted above, both the subcutaneous tissue and muscle tissue have been commonly used as sites for administration of pharmaceutical substances. The dermis, however, has rarely been targeted as a site for administration of substances. This may be due, at least in part, to the difficulty of precise needle placement into the intradermal space. Furthermore, although the dermis, and in particular the papillary dermis, has been known to have a high degree of vascularity, it has not heretofore been appreciated that one could take advantage of this high degree of vascularity to obtain an improved absorption profile for administered substances compared to subcutaneous administration. This is because small drug molecules are typically rapidly absorbed after administration into the subcutaneous tissue which has been far more easily and predictably targeted than the dermis has been. On the other hand, large molecules such as proteins and large polypeptides are typically not well absorbed through the capillary epithelium regardless of the degree of vascularity so that one would not have expected to achieve a significant absorption advantage over subcutaneous administration by the more difficult to achieve intradermal administration even for large molecules.

Numerous methods and devices have been proposed to enhance the permeability of the skin and to increase the diffusion of various drugs through the skin to be utilized by the body.

Devices for Skin-Based Delivery

Recent advancements in microelectrical mechanical systems (MEMS)-based fabrication technologies have permitted the development of small needle-like devices that overcome this tissue barrier and provide direct mechanical access to the epidermis and upper dermal tissue. Minimally-invasive safe delivery is accomplished by limiting the depth of penetration to the outer 10 µm to 2 mm, thus avoiding the nerve endings and blood vessels found deeper within the skin. Micro-cannula- and microneedle-based methodology and devices are described in U.S. application Ser. No. 606,909, filed Jun. 29, 2000. Standard steel cannula can also be used for intra-dermal delivery using devices and methods as described in U.S. Ser. No. 417,671, filed Oct. 14, 1999. These methods and devices include the delivery of substances through narrow gauge (30 G or narrower) "micro-cannula" with a limited depth of penetration (typically ranging from 10 µm to 2 mm), as defined by the total length of the cannula or the total length of the cannula that is exposed beyond a depth-limiting hub feature.

The devices for disrupting the stratum corneum include microabraders and microsize needles or blades having a length to penetrate and substantially pierce the stratum corneum. Other devices include microabraders and microsize needles or blades having a length to penetrate the stratum corneum without substantially piercing the stratum corneum. Microneedles include structures with a diameter equivalent to or smaller than about 30 gauge, typically about 30-50 gauge when such structures are cylindrical in nature. Non-cylindrical structures encompassed by the term microneedles would therefore be of comparable diameter and include pyramidal, rectangular, octagonal, wedge, and other suitable geometrical shapes. Examples of these devices are disclosed in U.S. Pat. No. 5,879,326 to Godshall et al.; U.S. Pat. No. 5,250,023 to Lee et al., and WO 97/48440.

Pharmacokinetics

Comparative studies have shown that the pharmacokinetic (PK) profiles of medicaments delivered to particular compartments of skin and depths within those compartments can vary dramatically. For example, pharmacokinetics for certain classes of medicaments can be improved by intradermal delivery (see, e.g., U.S. application Ser. No. 606,909 filed Jun. 29, 2000 and U.S. application Ser. No. 893,746 filed Jun. 29, 2001 (Published Jul. 18, 2002 as publication no. 20020095134)). To date the focus of altering PK through intradermal delivery has been on increased onset of effect and enhanced bioavailability relative to standard SC dosing.

SUMMARY OF THE INVENTION

The present invention pertains to methods and devices for controlling the pharmacokinetics of administered drug substances by combining the advantages of delivery to two or more compartments or depths within skin. In particular, the invention provides a method for delivering a substance to the shallow SC and ID compartments to achieve a hybrid pK profile that has a portion similar to that achieved by ID delivery and another portion similar to that achieved by SC delivery. This provides rapid and high peak onset levels of the compound as well as a lower prolonged circulating level of the compound.

This objective can be accomplished for example, by
(a) fluid overloading of the deep ID space;
(b) deposition at the ID/SC junction; and
(c) single or multiple microneedles targeting the different locations in the skin, i.e. the shallow ID space and the shallow SC space.

Thus, the present invention provides for a method for delivering a therapeutic substance into tissue comprising delivering the substance within or beneath the skin at least into the intradermal space to access two or more compartments or depths, which compartments or depths afford the substance different pharmacokinetics, which enhance the effectiveness of the substance in terms of a resultant composite pharmacokinetics. Access to two or more compartments may be achieved by independent delivery to two or more depths or compartments, or by using methods of delivery that target the tissue at the interface of two compartments, or that overload one compartment such that the delivered substance enters a second compartment by, for example, diffusion.

By ID compartment is meant the tissue space consisting of the dermal layer beginning immediately below the epidermis and extending to the base of the reticular dermis. On average this tissue depth is from approximately 0.05-0.15 mm to approximately 1.7-2.5 mm below the outermost skin surface. One skilled in the art will recognize that there is some variability in the absolute thickness and depth of the dermal compartment based on individual biological variability associated with age, race, body site, certain disease states, and other factors.

By SC compartment is meant the tissue space immediately below the reticular dermis and extended to the underlying muscle. On average, this tissue space begins at a depth of approximately 1.7-2.5 mm below the outermost skin surface, and has a lower depth that is highly variable with physiological factors including body mass index, degree of thinness or obesity, body site, age, race, certain disease states, and other factors.

The present invention further provides for a method where the substance is delivered to a site or sites that include two or more compartments.

The present invention also provides for a method where the substance is delivered to multiple sites that each include one or more compartments.

The invention further provides for controlled delivery of a substance using algorithms having logic components that include physiologic models, rules based models or moving average methods, therapy pharmacokinetic models, monitoring signal processing algorithms, predictive control models, or combinations thereof.

The present invention provides a method for combinations of shallow SC and ID delivery to achieve improved PK outcomes. These outcomes are not achievable using solely one delivery compartment or another. Individual or multiple site deposition via proper device configuration and/or dosing method may obtain unique and beneficial results. The utility of combining the effects of controlled shallow SC and ID delivery of substances using needles are previously unreported.

Devices for use with these methods can be configured to achieve both SC (or IM) and ID delivery.

The underlying technical principle is that the PK outcome of microneedle delivery is specific to the deposition depth and patterning of the administered fluid, that such deposition can be controlled mechanically via device design and engineering or by technique such as fluid overloading of the ID space.

In addition, the invention includes needles (micro or otherwise) for SC injection having a length less than 5 mm length. Shallow SC delivery to a depth of about 3 mm yields almost identical PK to deep SC using traditional techniques. The utility of shallow SC delivery alone to yield more controlled profiles has never been exploited. In fact, previously depths of less than 5 mm have been considered to not be within the SC space.

Mixed delivery either by device design or technique results in biphasic or mixed kinetic profiling. Minor differences in device length (1 mm vs. 2 mm vs. 3 mm) yield dramatic differences in PK outcomes. SC-like profiles can be obtained with needle lengths often assumed to locate the end of the needle within the ID space. Shallow SC delivery is more consistent and uniform in PK outcomes than standard SC delivery.

For substances that are administered by injection, the limits of the targeted tissue depth are controlled inter alia by the depth to which the needle or cannula outlet is inserted, the exposed height (vertical rise) of the outlet, the volume administered, and the rate of administration. Suitable parameters can be determined by persons of skill in the art without undue experimentation.

Examples of substances that may be delivered in accordance with the present invention include pharmaceutically or biologically active substances including diagnostic agents, drugs, and other substances which provide therapeutic or health benefits such as, for example, nutriceuticals. Potential diagnostic substances useful with the present invention include macromolecular substances such as, for example, inulin, ACTH (e.g. corticotropin injection), luteinizing hormone-releasing hormone (eg., Gonadorelin Hydrochloride), growth hormone-releasing hormone (e.g. Sermorelin Acetate), cholecystokinin (Sincalide), parathyroid hormone and fragments thereof (e.g. Teriparatide Acetate), thyroid releasing hormone and analogs thereof (e.g. protirelin), secretin and the like.

Therapeutic substances that may be used with the present invention include Alpha-1 anti-trypsin, Anti-Angiogenesis agents, Antisense, butorphanol, Calcitonin and analogs, Ceredase, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormone antagonists, Hirudin and Hirudin analogs such as Hirulog, IgE suppressors, Insulin, insulinotropin and analogs, Insulin-like growth factors, Interferons, Interleukins, Luteinizing hormone, Luteinizing hormone releasing hormone and analogs, Heparins, Low molecular weight heparins and other natural, modified, or syntheic glycoaminoglycans, M-CSF, metoclopramide, Midazolam, Monoclonal antibodies, Peglyated antibodies, Pegylated proteins or any proteins modified with hydrophilic or hydrophobic polymers or additional functional groups, Fusion proteins, Single chain antibody fragments or the same with any combination of attached proteins, macromolecules, or additional functional groups thereof, Narcotic analgesics, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, Thrombolytics, Tissue plasminogen activators, TNF-, and TNF-antagonist, the vaccines, with or without carriers/ adjuvants, including prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, addiction, arthritis, cholera, cocaine addiction, diphtheria, tetanus, HIB, Lyme disease, meningococcus, measles, mumps, rubella, varicella, yellow fever, Respiratory syncytial virus, tick borne japanese encephalitis, pneumococcus, streptococcus, typhoid, influenza, hepatitis, including hepatitis A, B, C and E, otitis media, rabies, polio, HIV, parainfluenza, rotavirus, Epstein Barr Virus, CMV, chlamydia, non-typeable haemophilus, moraxella catarrhalis, human papilloma virus, tuberculosis including BCG, gonorrhoea, asthma, atheroschlerosis malaria, *E-coli*, Alzheimer's Disease, H. Pylori, *salmonella*, diabetes, cancer, herpes simplex, human papilloma and the like other substances including all of the major therapeutics such as agents for the common cold, Anti-addiction, anti-allergy, anti-emetics, anti-obesity, antiosteoporeteic, anti-infectives, analgesics, anesthetics, anorexics, antiarthritics, antiasthmatic agents, anticonvulsants, antidepressants, antidiabetic agents, antihistamines, antiinflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, and sexual hypofunction and tranquilizers.

Substances may be delivered by bolus, metered bolus or infusion, with bolus and metered bolus delivery being preferred.

BRIEF DESCRIPTION OF THE DRAWINGS

FIG. 7 A-D show schematic diagrams of exemplary configurations of injection devices. Path of administered fluid is shown by arrows.

DETAILED DESCRIPTION OF THE INVENTION

Figure 1A:
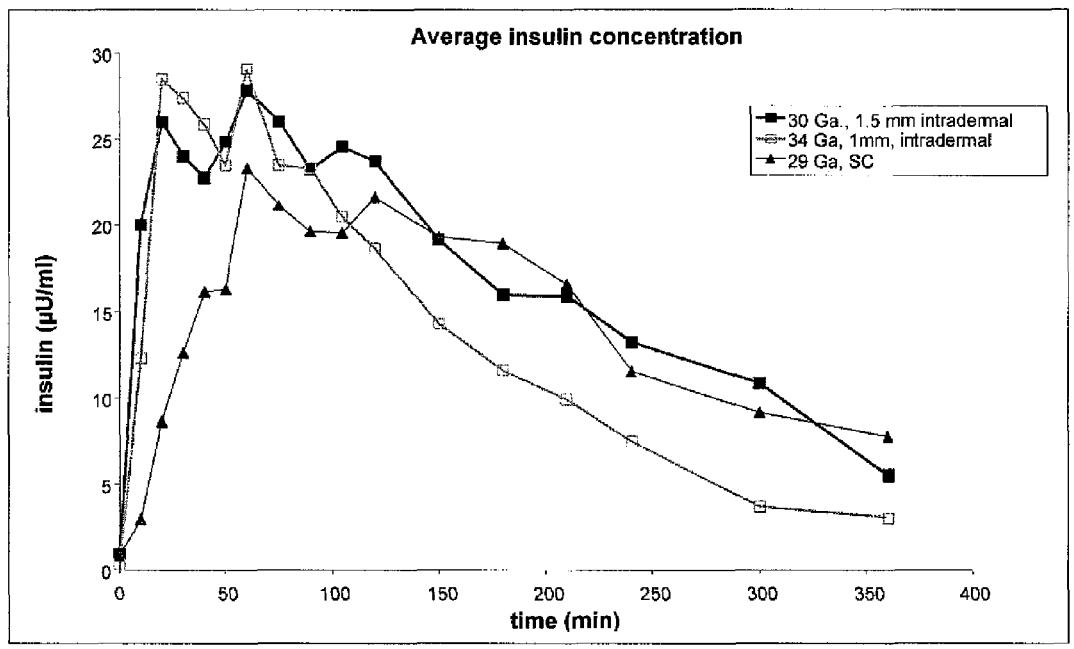
FIGS. 1A and 1B show average glucose concentration over time after delivery of insulin into skin at two different ID depths and one SC depth. For SC injection, a 29 Ga, 12.7 mm standard insulin syringe and needle were used with a pinch up technique.

Previous studies with intradermal delivery using microdevices demonstrated that intradermal delivery of many drugs, especially proteins, large polypeptides or other large molecular weight drugs, results in faster onset of uptake from the administration site, more rapid systemic distribution, in some cases increased bioavailability, but no change in intrinsic biological clearance mechanisms or rates. In several studies it was demonstrated that altering the depth of microneedles and therefore their tissue deposition space alters the PK of those drug entities. This observation has been repeated with a number of substances, such as recombinant protein hormones, both in preclinical animal trials in swine and in humans with recombinant human insulin.

Deposition in the shallow ID tissue space results in faster drug onset kinetics for systemic uptake and availability, and increased availability for some drugs. ID delivery is limited by the fact that the ID tissue space is highly compact consisting of highly structured collagen/elastin matrix, minimally distensible (compared to SC), and has limitations on the amount of total volume that can be administered, the rate at which such fluid can be administered, and the pressure required to administer such volume.

The SC space (layer) is principally located between the dermal space on one side and muscle or other fascial planes on the other side. Unfortunately this space is not nearly as well perfused by capillaries (both vascular or lymphatic) as the dermis, so absorption is both slower and in some cases less bioavailable. Also the SC layer has extreme variability intra-individually based on physical location (e.g. arm, abdomen, buttocks) and inter-individually based on physiological morphology (thin, normal, obese). Current delivery practices such as injections, jet injections and infusions into the SC layer result in highly variable deposition of therapeutic compounds such as proteins, peptides and other molecules even within a single individual at a single dosing site. This leads to highly variable absorption of these compounds and as a result may unfavorably alter drug efficiency. Direct deposition of drugs into the shallow SC space i.e., to the depth of less than 5 mm, or more preferably to a depth of less than 3 mm or even more preferably to a depth of between 2 and 3 millimeters allows the ease of SC dosing, and achieves greater consistency of pharmacokinetics versus the use of standard longer needles and standard practices described above.

Standard SC dosing has also often been thought to be limited by an upper boundary within which ID deposition is thought to occur. This upper boundary has been defined by published patents and other publications for compounds such as insulin as being 5 mm in depth. This is also reflected in current products (e.g. insulin syringes and pen needles that have a minimal length of 5 mm, see also U.S. Pat. No. 6,200,296 B1, Dibiasi et al.). New data suggest that in animal models shallower deposition of only 3 mm yields not only equivalent SC profiles to standard techniques but also better reproducibility of drug kinetics.

The thickness of the dermis and epidermis varies from individual to individual, and within an individual, at different locations on the body. For example, it has been reported that the epidermis varies in thickness from about 40 to about 90 µm and the dermis varies in thickness ranging from just below the epidermis to a depth of from less than 1 mm in some regions of the body to just under 2 to about 4 mm in other regions of the body depending upon the particular study report (Hwang et al., *Ann Plastic Surg* 46:327-331, 2001; Southwood, *Plast. Reconstr. Surg* 15:423-429, 1955; Rushmer et al., *Science* 154:343-348, 1966). This variation must be taken into account when the depth(s) of delivery at particular sites are determined. Currently some preferred sights for drug administration include but are not limited to the thighs, abdomen, buttocks, chest region, and various aspects of the arm including bicep, tricep, deltoid, and forearm.

In the locations mentioned above, which have been customarily used in the prior art, ID injections to a depth of about 1.7 mm to 2.5 mm deposit drugs within both the ID and SC layers of the skin. Drug is deposited both in the lower ID and most shallow SC regions. Alternatively needles with a length to deposit substances within the ID space (less than 1.7 mm nominally) can be made to overload the targeted tissue space with injected fluid. When this occurs, the deposited materials or drug solutions partition within both the lower ID and SC space. This result occurs most readily with longer ID needles, as the lower ID tissue bed is composed of more distensible tissue than the upper dermis, and the injected fluid follows the path of least resistance.

This mixed deposition yields unique pharmacokinetic parameters compared to SC or ID deposition alone. Absorption from the ID space still occurs more rapidly leading to faster onset of systemic availability ($T_{max}$), but without the dramatic concentration peaks ($C_{max}$) previously seen in very shallow dermal delivery. (See U.S. application Ser. No. 606,909, filed Jun. 29, 2000.) Because of the close proximity to venous and lymphatic capillaries where absorption can occur and reduced need of perfusion through the poorly perfused SC tissue bed, drug absorption is more rapid and reproducible than deeper SC administration. This mixing of pharmacokinetic outcomes can be exploited for further tailoring of desired pharmacokinetic profiles. These "biphasic" profiles can be used for example with insulin and recombinant protein hormones.

In recent human clinical trails with ID delivery of regular U-100 human insulin in the thighs of volunteers, pharmacological benefit was obtained over standard SC injection in the abdomen with standard gauge needles and techniques. Insulin was delivered with a 30 g 1.5 mm needle, 34 g 1.0 mm or standard SC (29 Ga, 12.7 mm) needle, and blood glucose and insulin levels measured using standard techniques, and blood glucose was maintained at a constant level using glucose clamp techniques. The pharmacodynamic response of blood glucose reduction, as reflected by the rate of glucose infusion required to maintain glucostasis, occurred more rapidly for ID injection than with SC injection. This is in good agreement with previously obtained pre-clinical results in swine. The blood insulin levels in humans did not show as dramatic peak concentrations ($C_{max}$) significantly higher than SC, however the onset of detectable blood insulin levels ($T_{max}$) was increased. Likewise, with ID systems average profiles tend to show a biphasic response with both early and later phase absorption. This is indicative of drug partitioning between the different tissue layers (ID and shallow SC) and combining of the PK absorption parameters of each. This is also more reflective of native insulin secretion, which exhibits both acute high levels of secretion and longer low levels of secretion to cover both peak, and prolonged carbohydrate metabolism.

Biphasic kinetics are expected to be applicable to a wide range of medicaments. These medicaments include those drugs whose desired profile dictates both a rapid onset of action followed by lower but longer circulating levels of drug. In addition, any substance delivery profile produced by cells in this regard could be replicated. Preferred drugs include but are not limited to:

Insulin. Rapid and high peak onset levels to cover the high glucose levels obtained from digestion and absorption of simple sugars or other non-complex carbohydrates, and rapidly brings blood glucose back to "normal" level. Secondary low insulin levels cover complex carbohydrate metabolism, but reduce the risk of hypoglycemia due to lower circulating levels of insulin. This combined PK outcome is currently achieved mechanically using only expensive and complex insulin pumps, or by mixing formulations of different insulin types such as 70/30 mixtures.

Hormones, for example growth hormones, are naturally secreted in pulsatile fashion by the body. This pulsatile profile when mimicked by IV administration may result in minimal to no positive outcome. For therapeutic applications SC delivery with low circulating levels may be optimal for physiological responses. Bimodel or biphasic kinetic outcomes for hormones could achieve optimal results heretofore unobtainable due to the pharmacokinetic limitations of current formulations, dosing regimens and delivery techniques.

Pain relief agents (e.g. for migraine, cancer, or post-operative pain) such as COX inhibitors, morphine, opioids, other narcotic analgesics, triptans, etc. Pain relief agents typically require rapid onset of effect attainable by shallow ID delivery but lower prolonged circulating levels of drug to prevent pain recurrence. Currently, to obtain high peak levels typically requires larger drug quantities to hit peak levels, which then results in prolonged high circulating levels. This prolongation of high circulating drug levels is often responsible for deleterious side effects such as GI effects for COX drugs, or the loss or cognitive or functional ability for narcotic analgesics. By mixing kinetic profiles high peak levels may be obtained to generate pain relief, while minimal circulating levels can be maintained to prevent pain recurrence, but minimize side effects. Similar effects may be expected for drugs with high toxicity levels, such as chemotherapeutic agents.

Erectile dysfunction agents. Rapid onset is desirable, but extended duration of effect may also be desired. This can be obtained via biphasic or bimodal kinetic profiling.

High molecular weight or hydrophobic drug compounds (e.g. monoclonal antibodies or narcotics such as fentanyl): For traditional SC administration high molecular weight drug agents are only slowly absorbed since absorption is typically an inverse function of molecular weight. For hydrophobic agents partitioning into and binding to tissue delays absorption. A combined kinetic profile speeds the onset of effect by making the drug readily available early, and provides depots for continuous effect.

Anti-clotting factors (e.g. heparin). High early peak levels are desirable to dissolve clots or thrombi that have already occurred but high levels are not desirable over the long term due to side effects. This can be obtained via biphasic or bimodal kinetic profiling.

Operative Variations and Alternatives

Drug Entity. Multiple entities and classes of agents can be used in the invention. Particularly preferred are the agents mentioned in the previous section. Other suitable agents can be determined by those of skill in the art using routine experimentation.

A number of different methods can be used to assure bimodal or biphasic kinetics. All methods rely on partitioning of drug between two distinct tissue areas (ID and shallow SC) with different absorption characteristics. The exact delivery depth needed may be variable between dosing sites or patient populations but can be readily determined experimentally using techniques such as punch biopsy or non-invasive means such as fluoroscopy.

Fluid overloading of the deeper ID space using "longer" ID devices is the easiest technique to perform. However, it may have higher degree of variability associated with it. Deposition patterning can also vary with this approach and could vary with the actual technique employed. As used herein, the term "deposition patterning" refers to depositing substances at one or more sites, with each site being within one or more tissue compartments. This could be valuable for drugs that have less need for tight control or have a broad therapeutic window (e.g. pain relief, hormones). This approach is clearly dependent on fluid volume and or delivery rate and therefore optimization would, in large measure, be empirically determined. By maintaining fluid volumes and rates within specified ranges variability may be minimized. Direct deposition using a single microneedle of a length specific to the dermal/SC junction. This method appears at the outset to be more controllable than the method above and is likely to be more mechanically reliable since it employs device specific control. However since deposition occurs at a junction of two distinct regions of absorption, there could be some biological variability, with some injections having a greater contribution from ID kinetics and others a greater contribution from SC kinetics. Based on existing data, this approach is expected to be best for compounds that do not require the high early Cmax values. There may also be a regulatory benefit since there exists a similarity to standard SC injections, which may be similar enough to assert "bioequivalence" for regulatory approval. Examples include certain hormones and heparins.

Another method involves multiple microneedles targeting distinctly different tissue compartments. An example of this approach is the use of a combined 2 needle array consisting of a 1 mm microneedle and a 3 mm microneedle. This system will result in the greatest deposition accuracy since each microneedle distinctly targets the individual tissue compartments. This method may provide the most controllable pharmacokinetic profiles since substance deposition in the ID and SC compartments is more likely.

Another approach involves a single microneedle with multiple lumens or outlets: Examples of an appropriate device useful in this approach would include a sprinkler needle with outlets at 1 and 3 mm or dual lumen systems with a similar design concept. Each microneedle would have its own unique fluid mechanics, biomechanics or deposition properties. Such properties would be readily determined without undue experimentation by one skilled in the art.

Device Configuration:

An appropriate delivery system would be one capable of providing deposition patterning and further providing for PK control mechanism or means so that the kinetics of the therapeutic substance can be optimized. Such a control mechanism or means would optimally involve feedback control. Optimization is expected to be experimentally determined. Possible delivery systems include catheter, pens, patch pumps, ballistic injection devices, iontophoretic or electrochemical devices, etc, integrated with control means. It is within the scope of the present invention for the use of a plurality of devices used independently of each other to provide for the deposition patterning. Thus, by way of example, one device may be used to deliver substance to one compartment either serially or simultaneously with another device, of same or different configuration, to deliver to another compartment. Delivery of complimentary or cooperative therapeutic substances, serially or simultaneously, by one or more devices, by the method of the present invention is also feasible if so desired.

If reservoirs or flowpaths are combined, deposition may be complex due to fluid mechanics. One important factor to be considered is that longer needles reach more readily distensible tissue with lower back pressure to fluid administration so that longer needles become the path of least resistance to the administered drug. Thus, devices having multiple needles or needles having multiple outlets must be configured so that the fluid is delivered in the desired proportion to each location.

Examples of suitable devices include independent devices with independent reservoirs and flow paths to target different depths; a single device incorporating dual reservoirs, each feeding an independent flow path of different depth; a single reservoir with heterogeneous needle lengths; a device having one manifold and two needles that incorporates a valving or backpressure device to equilibrate pressure and/or fluid flow; a device having one manifold and two needles of different lengths and diameters to equilibrate delivery; a device having one tapered needle or cannula with two or more orifices, wherein orifice diameter and taper are adjusted to equilibrate delivery; a device with a cannula having a multiplicity of ports at a shallow level with a greater total outlet area than a lower level port; a device with a cannula having a shallow level port and a tortuous pathway to a lower level port; a device having a single extendible/retractable needle capable of depositing fluid sequentially at two different depths; a device that delivers fluid to the interface of two spaces (e.g. ID and SC).

Variability of Volume Deposition:

The amount of drug delivered to each site can be controlled through appropriate fluidic plumbing of such device. The resultant kinetic profile will resemble the additive profile from each site-specific compartment.

Effect of Duration of Delivery:

Patterned deposition is dependent upon delivery rate to the site and is most relevant to bolus/metered bolus delivery. (As used herein, "metered bolus delivery" refers to delivery that occurs within a time frame of 15 minutes or less at a specific rate.) Under these circumstances, uptake from the site has limited time to occur during the actual delivery period. By comparison, during prolonged infusions, the drug begins to be absorbed from the delivery site while administration to that site is still occurring.

EXAMPLE 1

Pharmacokinetic Fits and Physiological Models for Intradermal Insulin Delivery Profiles from Human Clinical Trials In order to investigate the pharmacokinetic and pharmacodynamic effects of human insulin administered intradermally at different depths to the skin, experiments in human volunteers were carried out with two microneedle delivery systems. Fifteen healthy male volunteers (age 28.3±5.4 years, BMI 24.2±2.6 kg/m² (mean±SD)) received 10 U human insulin via 2 different microneedles of 1.0 and 1.5 mm lengths, and 10 U via standard SC administration. ID microneedle injection was given utilizing a 30 Ga, 1.5 mm microneedle as a rapid bolus in the upper thigh over approximately 10 sec duration; ID microneedle infusion was given using a 34 Ga, 1 mm microneedle infusing into the upper thigh at a rate of 100 microliters/min for a 2 min total duration; SC administration was in the abdomen using a standard 29 Ga, 12.7 mm insulin syringe. Glucostasis was maintained at a continuous preset level under euglycemic glucose clamp conditions using automated instrumentation (target blood glucose level 5.0 mmol/L, continuous i.v. insulin infusion of 0.15 mU/kg/min to suppress endogenous basal insulin secretion, clamp duration 360 min post-dosing). Blood samples were withdrawn at standardized timepoints to confirm BG values, and for insulin and C-peptide quantitation.

Figure 1B:
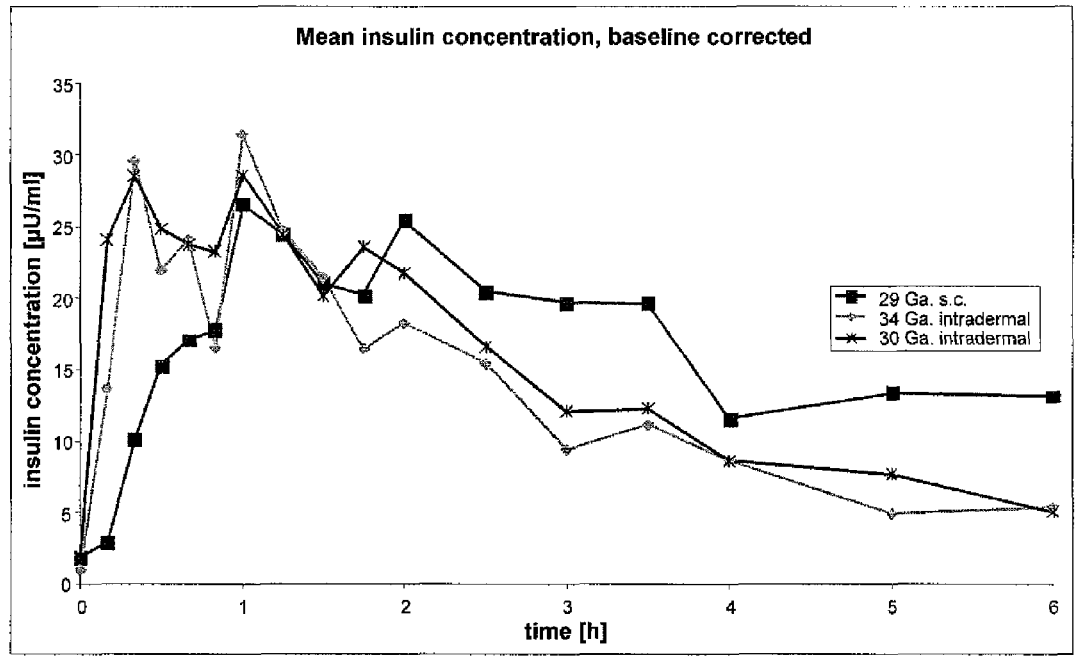

The results of human clinical trials show good correlation to the effects seen pre-clinically in animal trials. The onset of systemically available insulin is increased and the onset for blood glucose effects is also more rapid. FIG. 1 shows average blood insulin values (n=55) for patients receiving ID insulin via either microneedle configuration and SC regular insulin. Values were adjusted for baseline background. Tmax for ID insulin is significantly shorter than the relative SC control condition.

Figure 2:
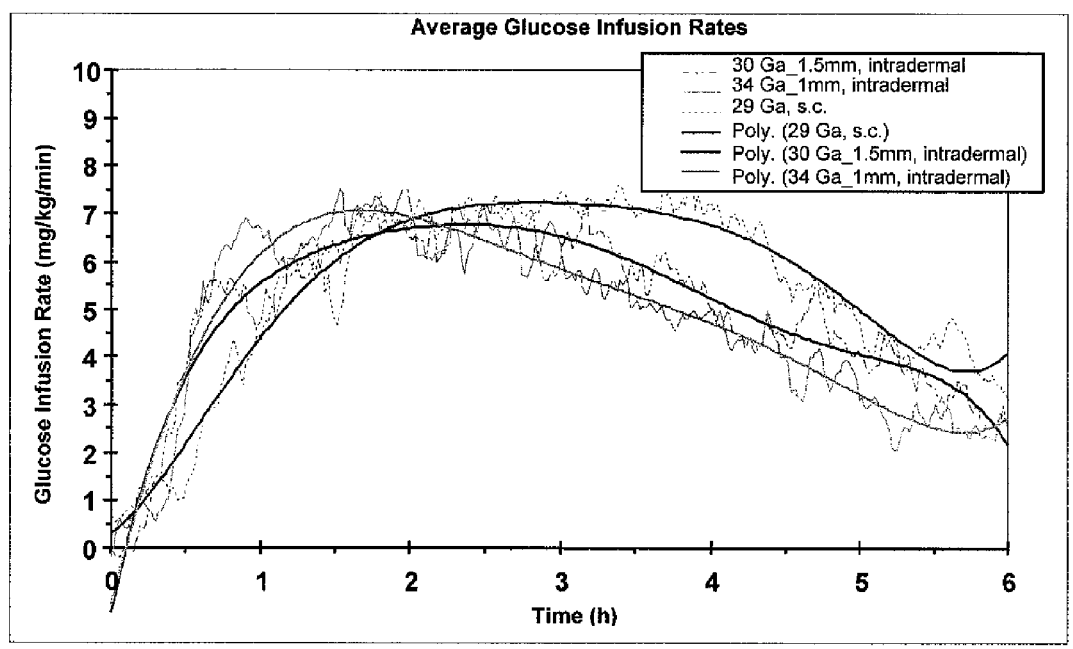
FIG. 2 shows average glucose infusion rates under glucose clamp conditions with ID and SC administration of insulin.

Under glucose clamp conditions, additional IV glucose must be infused as insulin metabolism occurs. FIG. 2 shows that with ID administration, increased glucose infusion rates are needed significantly earlier than with SC. FIG. 2 represents average glucose infusion rates for all delivery conditions, and best fit polynomial curves (solid lines) for all infusion rates. Although the maximal effect on required glucose administration rate (Teff$_{max}$) is similar for ID and SC, this maximal effect is reached in approximately one-half the time via the ID route (see Table 1). In fact significant glucose reduction (Teff$_{50\%}$) occurs within 30 minutes of administration. Again, these response data are in good agreement with the PK uptake data.

As shown in Table 1, microneedle delivered insulin showed a faster onset of action compared to SC as indicated by lower values for t$_{INS-max}$ and AUC$_{INS-0-60}$.

TABLE 1

|  | SC | 1 mm | p* | 1.5 mm | p* |
|---|---|---|---|---|---|
|  | PK | | | | |
| t$_{max}$ (min) | 132.0 | 42.5 | <0.0001 | 67.0 | <0.05 |
| % AUC$_{tot}$ @ 1 h | 13.2 | 28.2 | <0.0001 | 22.3 | <0.0001 |
| C$_{max}$ (µU/mL) | 17.2 | 24.4 | <0.05 | 22.0 | <0.05 |
| F (% vs SC) | 100 | 97 | — | 114 | — |
|  | PD | | | | |
| t$_{50\% eff-max}$ (mm) | 56 | 31 | <0.0001 | 32 | <0.0001 |
| t$_{eff-max}$ (min) | 209 | 109 | 0.0003 | 157 | N.S. |
| GIR$_{max}$ (mg/kg/min) | 7.86 | 7.40 | N.S. | 7.34 | N.S. |

*Bonferroni/Dunn Test

In contrast to other insulin delivery methods such as iontophoretic delivery, inhalation, and oral dosing, the relative bioavailability (F) of microneedle administered insulin was very similar to SC. Also, microneedle pharmacodynamic measures showed a more rapid onset of action (t$_{50\% eff-max}$) and (t$_{eff-max}$) but a comparable maximal metabolic effect (GIR$_{max}$) when compared to SC injection. There were no adverse effects at any injection sites. Intradermal microneedle insulin injection were a safe and effective method for delivering insulin rapidly and completely. The rapid onset of the metabolic effect afforded by microneedle delivery offers great potential for prandial insulin administration.

A computational physiological compartmental model of insulin kinetics in a human patient was applied to a subset of the data (n=5 subjects) obtained from the human clinical trials to demonstrate the potential for occurrence of biphasic kinetics and possible methods to maximize its therapeutic utility. Subcutaneous data was well modeled using a single physiological input compartment. However, modeled fits to the intradermal data can only be achieved using input from at least 2 physiological tissue compartments. This reflects the biphasic (or potentially multiphasic) aspects of intradermal delivery with microdevices, which yield both pharmacologically beneficial results, and allow a control and predictive function not previously seen with other drug delivery systems.

In contrast to previous animal data for ID delivery of insulin, tThe intradermal delivery (ID) route displayed a unique "biphasic" behavior in humans. When compared to subcutaneous (SC) inputs, the ID delivery results in faster onset but also demonstrated an unexpected extended physiological clearance or decay, suggesting that multiple insulin uptake pathways were involved. A physiological based model of insulin uptake and distribution in diabetic patients (Parker, R. S., et al., 2000. Robust H-infinity Glucose Control in Diabetes Using a Physiological Model. AIChE J. 46 (12), 2537-2549; Sorensen, J. T., 1985. A Physiologic Model of Glucose Metabolism in Man and its Use to Design and Assess Improved Insulin Therapies for Diabetes. PhD Thesis, M.I.T) was utilized to fit the averaged experimental data (n=5 test subjects) and determine which parameters best represented the measured insulin absorption.

The model allows insulin input into any physiological compartment, and peripheral tissue was chosen to approximate the skin and subcutaneous tissue. A 1-minute input duration for bolus insulin delivery was selected to simplify calculations. This input also effectively represents the ID delivery methods used in human clinical trials, which were either a rapid bolus over approximately ten seconds or an equivalent dose over a 2-min duration. The basic response of the model to a peripheral tissue input shows the body responds rapidly to the bolus input showing complete uptake and distribution within 5 minutes, and complete insulin clearance within 70 minutes. This result is also in good agreement with ID delivery data previously obtained in diabetic animal models.

To model the SC input, a delivery route involving a delayed input into the body is required, since the detectable onset of the drug is much later than the peripheral model alone allows. This modeling input is an effective representation of the accepted uptake pathway for regular human insulin. The added components represent transformation of the unabsorbable hexameric form of insulin dissociating to the bioavailable monomeric and dimeric forms of insulin. The model response closely matches the experimental data. The rates of transformation are first order. Dissociation is routinely considered to be the rate-limiting step for bioavailability from the SC tissue compartment.

The same subcutaneous delivery model, when applied to the ID data (1.5 mm delivery data) fails to match the data's behavior. The subcutaneous model system fails to capture the short onset time and rapid bioavailability observed from ID delivery. Likewise, the peripheral input model alone, fails to capture the extended decay seen in ID delivery.

In order to fit the observed ID data two delivery inputs are required. The first delivery input represents the rapid uptake from the peripheral dermal compartment and exhibits a faster rate constant. Previous ID delivery data (see U.S. Application Serial No. U.S. application Ser. No. 893,746 filed Jun. 29, 2001) in animal models demonstrated both the rapid onset and the lack of an equilibration step for hexameric insulin uptake from this compartment. The second delivery input represents the "slower" uptake from administered insulin that has entered the SC tissue compartment as a result of dosing technique or device design. Results of the mixed compartmental or "biphasic" model are well fitted to the ID profiles obtained. It is important to note that biphasic kinetics results from administration to two compartments, with each compartment exhibiting different uptake kinetics.

Refinements in the fitted model are also possible. Better approximations of the fast and slow absorption rate constants can be achieved by using other pharmacokinetic fitting methods. Likewise, the percentage distribution between the compartments can be determined experimentally by best fits of the absorption model, or designed ab initio prior to dosing based on device design and administration technique. Also additional compartments to represent different layers of the dermis with slightly different uptake may further refine the fit of the model system to the experimental data. However, with the current data these additional compartmental systems have not been shown to be statistically better than the above models.

The current fitted models are intended merely to demonstrate that the unexpected kinetic outcomes of human ID insulin delivery can be explained based on pharmacologically and physiologically acceptable models. Overall, it is clear that a single route of delivery is not adequate to explain the rapid initial onset and the extended decay of the ID data, whereas a single route is adequate to model the SC data. This unexpected observation of biphasic pharmacokinetics for human ID delivery has been previously observed in animal systems, but usually at deeper administration depths (approx. 2 mm). The fact that the biphasic (or bimodel) kinetics can be effectively fitted and physiologically modeled suggests that the dose administration can be tailored to unique pharmacokinetic endpoints not available with other dosing means. These PK endpoints can be effectively predicted and designed to yield effective pharmacological outcomes, and these endpoints can be effectively achieved in human dosing therapies using unique device configurations and dosing techniques. Such treatment affords the reliable controlled delivery of therapeutics to enhance their effectiveness and optimize their dosage amounts under a variety of conditions.

EXAMPLE 2

Preclinical Diabetic Swine Studies: Administration of insulin at various depths (1.5, 2.0 and 3.0 mm) Volumes and Concentrations 10 Units of insulin at different concentrations (U40-U400) were administered by bolus single microneedle administration to diabetic swine, and blood samples for insulin level quantitation and blood glucose were withdrawn at serial timepoints. Microneedles were depth limited 31 Ga, single-needle syringe based systems and administration was via manually controlled bolus over several seconds (approx. 5-15). Microneedle delivery depths included 1.5 mm, 2.0 mm, and 3 mm. Data are averages of n=5 or 6. Volumes for 10 IU administration for the different insulin concentrations are U40=250 uL, U50=200 uL, U100=100 uL, U200=50 uL, U400=25 uL. Volume delivery accuracy was insured via the use of calibrated glass microsyringes, and gravimetric quantification of any insulin which was not delivered.

Figure 3:
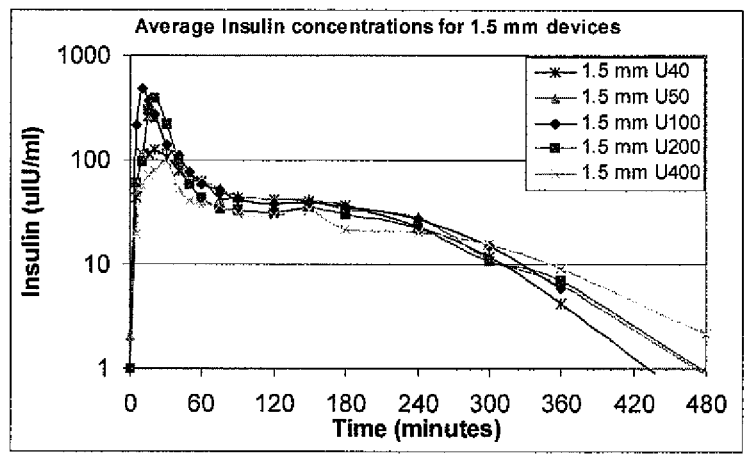
FIG. 3 shows a logarithmic plot of average blood insulin levels after administration of various insulin concentrations to diabetic swine using a 1.5 mm device.

Results:

Concentration/Volume effects at shallow depth (1.5 mm): Data for 1.5 mm administration of all concentrations are shown in logarithmic plots in FIG. 3. The logarithmic graph clearly shows the rapid uptake of insulin for all concentrations when administered by short microneedles to the shallow ID space. The majority of the AUC (area under the curve) is found at timepoints less than 45 minutes. Average Tmax values for all conditions were within the range 15-30 minutes. Differences in average max concentrations (Cmax) were observed, with low concentrations (U40 and U50) having reduced Cmax, and the highest concentration, U400 having dramatically reduced Cmax. This is consistent with the hypothesis that at higher volumes the local ID space "overfills" and exhibits spillover to the shallow SC. At exceedingly high concentration, the rapid onset effect is masked by a formulation effect. Highly concentrated insulin solutions such as U400 undergo self-complexation which limits uptake and distribution. This effect was also previously seen with U500 insulin (data not shown). We conclude that for single needle administration to the shallow ID space (<1.7 mm), volumes of approximately 100 uL or less allow primarily ID kinetics. Volumes greater than 100 uL begin to show an increased potential for biphasic character.

Figure 4:
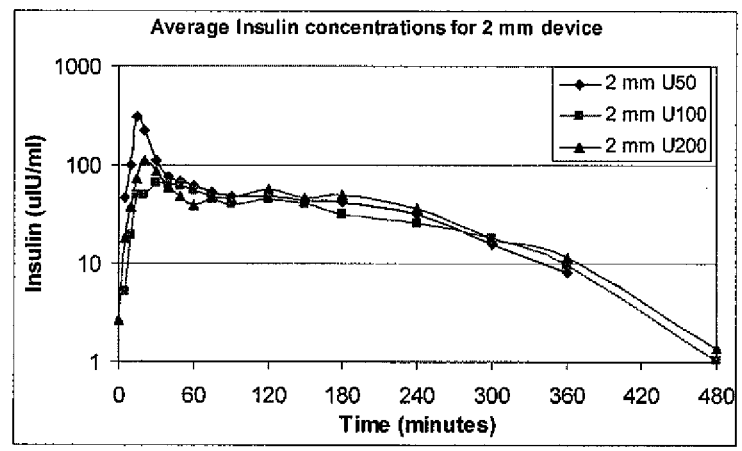
FIG. 4 shows a logarithmic plot of average blood insulin levels after administration of various insulin concentrations to diabetic swine using a 2.0 mm device.

Concentration/Volume effects at intermediate or interfacial depth (2.0 mm): Data for 2.0 mm administration of all concentrations tested are shown as a logarithmic plot in FIG. 4. In contrast to above data, the average graph shows rapid uptake of insulin for the lower insulin concentration, U50. However, this average graph is biased by two of the five individuals, which exhibited high peak values in the 15-20 minute time period. Average Tmax generally increased vs. more shallow delivery and were between 40-120 minutes. Again, average Tmax for the U100 delivery was biased by two individuals with high late phase absorption. Overall 2 mm delivery tended to exhibit reduced peak values, slightly longer onset times, and less AUC in the early time periods. At this administration depth low concentration/higher volume was the only condition to exhibit high peaks similar to shallow ID administration. This effect is believed to be due to a permeation effect wherein the interfacial deposition intrudes upward into the more shallow ID space.

We conclude that at this delivery depth both needle length and delivery volume are significant controlling factors for PK outcomes. Based on this data set, higher volumes maximize the potential for more rapid onset by swamping the interfacial space between the ID and SC tissue compartments and thus exhibit a increased potential for biphasic PK results. A moderate or larger volume of 100-250 uL per microneedle may likely yield the most reproducible PK outcomes.

Figure 5:
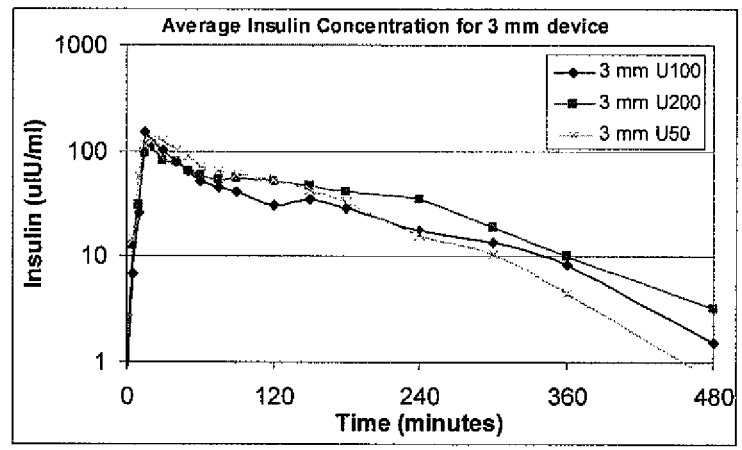
FIG. 5 shows logarithmic plots of average blood insulin levels after administration of various insulin concentrations to diabetic swine using a 3.0 mm device.

Concentration/Volume effects at deeper microneedle depth (3.0 mm): Data for 3.0 mm administration of all concentrations tested are shown in a logarithmic plot in FIG. 5. At this depth, PK profiles are minimally affected by volume and concentration. Average profiles are equivalent at all three concentrations tested. Average onset is still rapid with Tmax values between 20-55 minutes. Since it is expected that this depth falls completely within the hypodermis or subcutaneous space, the potential for obtaining biphasic kinetics from a single injection is limited. It is noted that the peak for uptake is more rapid than usually seen with standard SC.

We conclude that at this delivery depth, needle length overides volume and concentration effects. Consistency of delivery should still be greater than SC due to reduced technique dependence of administration and increased accuracy and reproducibility of drug delivery. Minor advantages in onset may occur simply due to the closer proximity of the depot to the dermis. This injection method could be combinable using a dual needle approach (at different needle depths) to obtain biphasic character.

EXAMPLE 3

Figure 6:
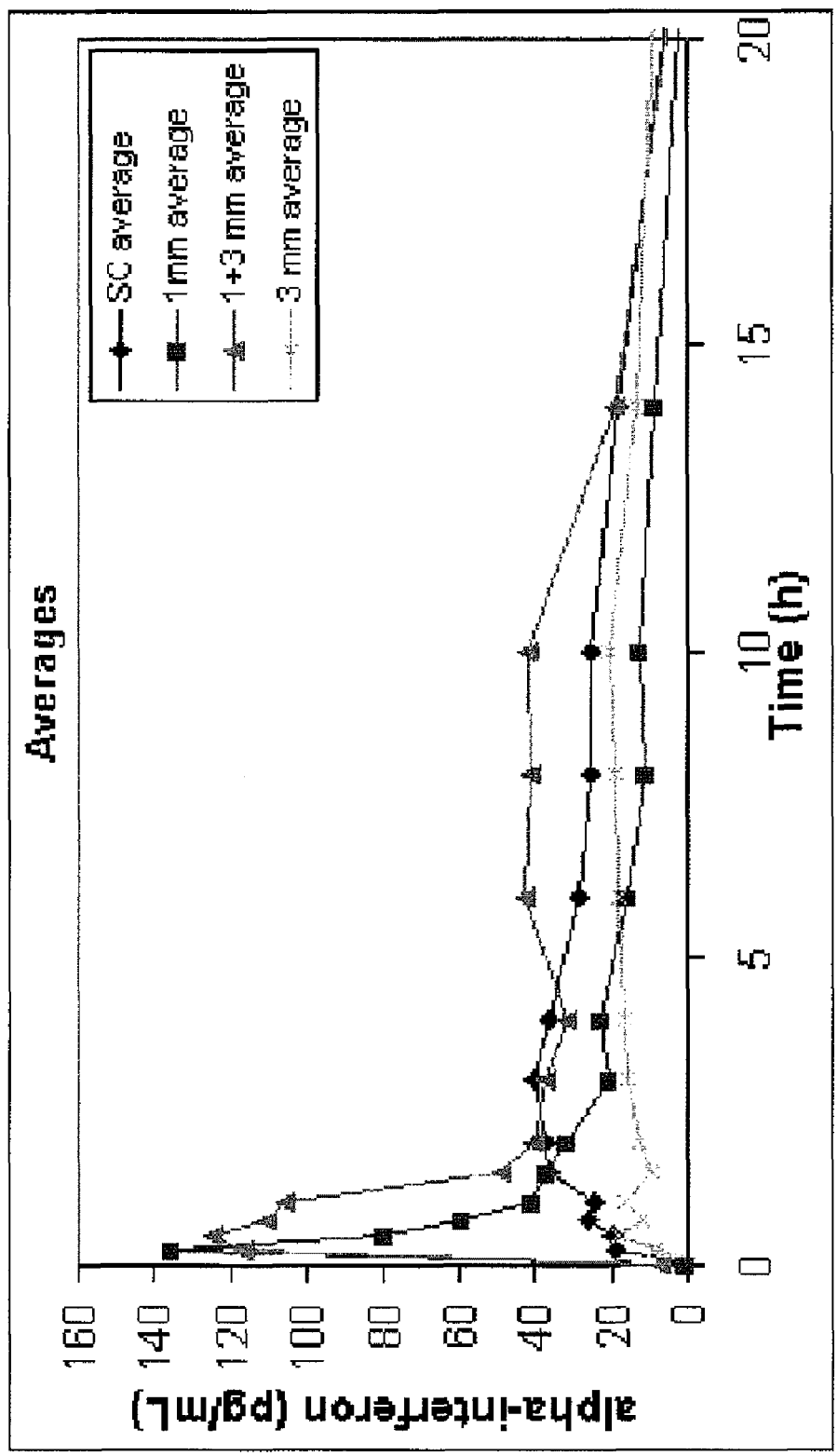
FIG. 6 shows blood alpha-interferon concentration over time after SC delivery and ID delivery at 1 mm and 3 mm depths, and the average for the two depths.
Figure 7A:
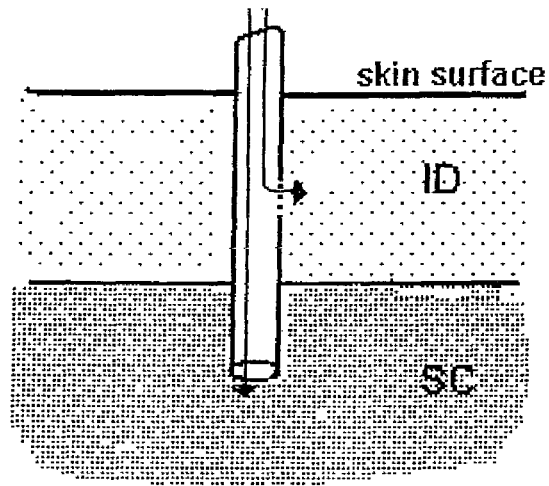
FIG. 7A shows a single needle with side and end ports configured such that the side port allows injection targeting the ID space and the end port allows injection targeting the SC space.
Figure 7B:
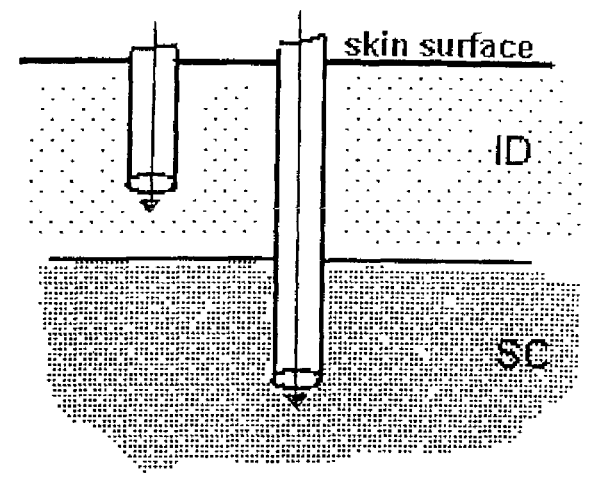
FIG. 7B shows a dual needle configuration such that one needle is positioned in the ID space and one needle is positioned in the SC space.
Figure 7C:
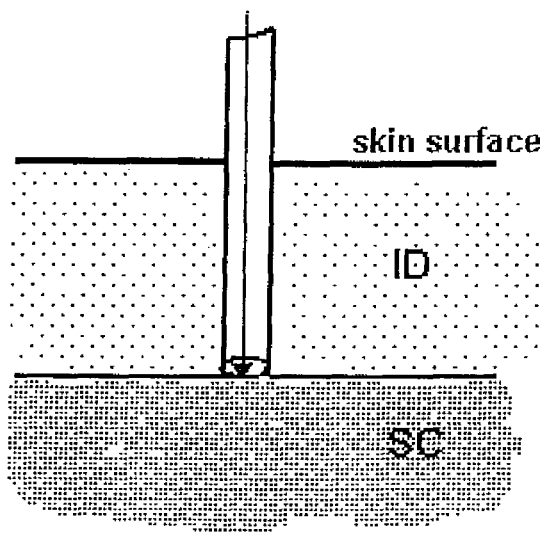
FIG. 7C shows a single needle positioned at the boundary of the ID and SC spaces, such that the substance injected targets both spaces.
Figure 7D:
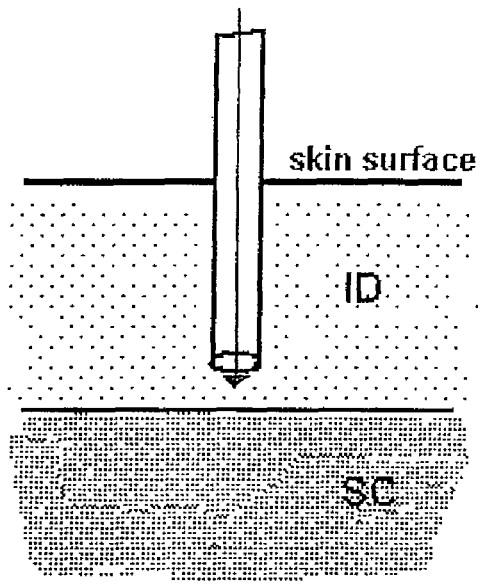
FIG. 7D shows a single needle positioned in the ID space such that fluid overloading will target both the ID and SC spaces.

Comparison of Delivery of α-Interferon Administered Simultaneously at Two Different ID This study was designed to demonstrate achievement of biphasic kinetics based on a specific mechanical design of the delivery device. In comparison to above examples which rely on simultaneous filling of multiple physiological compartments which are spatially related, this study was to investigate the resultant PK from independent filling of two physiological compartments. Interferon alpha (3 million IU in 0.2 mL; 15 million IU/mL concentration) was administered to swine via a single 34 Ga microneedle of either 1 or 3 mm length at a controlled rate of 50 μL/min. This dose was also administered via a standard SC injection from a 30 Ga, ½ inch needle, via a manual bolus (2-15 sec duration). In addition, 0.1 mL (half of the total dose) was delivered simultaneously through 34 Ga microneedles of both 1 and 3 microneedles at 50 μL/min. In this case the total dose remained constant (0.2 mL) but was split evenly between the two microneedle dosing sites which were within close physical proximity (approximately 1 inch apart). Average serum profiles (n=3-6) over time are shown in FIG. 6.

The 1 mm data show the expected PK outcomes for ID administration including extremely rapid onset, high Cmax, reduced Tmax, short systemic lifetime. SC and 3 mm profiles are similar showing slower onset of systemic availability, reduced Cmax, and more extended circulating lifetimes relative to the 1 mm delivery. In this example, the average concentrations and area under the curve (AUC) for 3 mm data were lower than expected. In contrast, the simultaneous delivery at two sites and splitting the dose between equivalently between both microneedle systems, shows both the dramatic peak onset and early absorption phase characteristic of ID delivery, and later phase absorption and longer circulating lifetimes characteristic of SC delivery. Unexpectedly, the total AUC resulting from combined administration at two sites appears greater than administration at a single site alone. One potential explanation for this may be that dividing the dosage may allow utilization of distinct uptake and distribution mechanisms at the different physiological sites. In contrast, the uptake mechanism for single site administration may be overloaded by the administered drug dose. This result may imply an additional beneficial outcome of controlled biphasic kinetic profiling.

These results show that PK of proteins such as alpha interferon can be advantageously controlled to yield benefits such as specific biphasic profiling and increased bioavailability using an administration means carried out according to the method of the invention.

Incorporation by Reference

To the extent necessary to understand or complete the disclosure of the present invention, all publications, patents, and patent applications mentioned herein are expressly incorporated by reference therein to the same extent as though each were individually so incorporated.

That which is claimed:

1. A method for delivering insulin to a subject comprising utilizing at least one delivery device to deliver insulin to the subject, wherein insulin is delivered to both the intradermal and the subcutaneous compartments, wherein the delivery device comprises a single needle or cannula, wherein the single needle or cannula comprises a side port that delivers insulin into the intradermal compartment, and wherein the single needle or cannula further comprises an end port that delivers insulin into the subcutaneous compartment, wherein the end port inserts into the subject's skin at a depth of at least about 2.0 mm to about 5.0 mm.

2. The method of claim 1, wherein delivery of insulin into the intradermal and subcutaneous compartments is essentially simultaneous.

3. The method of claim 1, wherein delivery of insulin into the intradermal and subcutaneous compartments is using algorithms having logic components that include physiologic models, rules based models or moving average methods, therapy pharmacokinetic models, monitoring signal processing algorithms, predictive control models, or combinations thereof.

4. The method of claim 1, wherein delivery of insulin into the intradermal and subcutaneous compartments is by a bolus injection.

5. The method of claim 1, wherein delivery of insulin into the intradermal and subcutaneous compartments is by a metered bolus injection.

6. The method of claim 1, wherein delivery of insulin into the intradermal and subcutaneous compartments is by an infusion.

7. The method of claim 1, wherein delivery of insulin into the intradermal and subcutaneous compartments is at a dose of 100-200μl.

* * * * *